(12) United States Patent
Pierskalla et al.

(10) Patent No.: US 12,115,001 B2
(45) Date of Patent: Oct. 15, 2024

(54) TISSUE PERFUSION SENSOR AND PLACEMENT DEVICE

(71) Applicant: ExoStat Medical, Inc., Prior Lake, MN (US)

(72) Inventors: Irvin T. Pierskalla, Prior Lake, MN (US); Kent R. Winger, Prior Lake, MN (US)

(73) Assignee: EXOSTAT MEDICAL, INC., Prior Lake, MN (US)

( * ) Notice: Subject to any disclaimer, the term of this patent is extended or adjusted under 35 U.S.C. 154(b) by 795 days.

(21) Appl. No.: 17/230,020

(22) Filed: Apr. 14, 2021

(65) Prior Publication Data

US 2021/0298632 A1 Sep. 30, 2021

Related U.S. Application Data

(63) Continuation-in-part of application No. 16/879,199, filed on May 20, 2020, now Pat. No. 11,013,434.

(Continued)

(51) Int. Cl.
*A61B 5/145* (2006.01)
*A61B 5/00* (2006.01)
*A61B 5/0537* (2021.01)

(52) U.S. Cl.
CPC ............ *A61B 5/682* (2013.01); *A61B 5/0537* (2013.01); *A61B 5/14542* (2013.01);
(Continued)

(58) Field of Classification Search
None
See application file for complete search history.

(56) References Cited

U.S. PATENT DOCUMENTS

| 4,207,160 A | 6/1980 | Frankenberger et al. |
| 5,763,762 A * | 6/1998 | Sweeney, Jr. .......... G01N 33/18 |
| | | 73/19.05 |

(Continued)

FOREIGN PATENT DOCUMENTS

| CN | 101023352 A | 8/2007 |
| CN | 107847868 A | 3/2018 |
| WO | WO-9219150 A1 * | 11/1992 ......... A61B 5/14542 |

OTHER PUBLICATIONS

Lu et al. "A High Precision, Fast Response, and Low Power Consumption in situ Optical Fiber Chemical pCO2 Sensor." Talanta. Jul. 15, 2008;76(2):353-9. Epub Mar. 15, 2008. (Year: 2008).*

(Continued)

*Primary Examiner* — Meredith Weare
(74) *Attorney, Agent, or Firm* — Fox Rothschild LLP

(57) ABSTRACT

A physiologic sensor for measuring the partial pressure of carbon dioxide is provided. The sensor includes a generally C-shaped in cross-section sensor cover, the sensor cover defining an opening on an underside thereof; a membrane body housed within the opening, the membrane comprising an amorphous fluoroplastic, the membrane including a first end and a second end and defines a chamber therewithin; a sensor body for coupling the membrane to the sensor cover; two or more electrodes positioned within the membrane chamber; and a substantially electrolyte-free liquid contained within the membrane chamber and in contact with the two or more electrodes.

20 Claims, 8 Drawing Sheets

Related U.S. Application Data

(60) Provisional application No. 62/915,164, filed on Oct. 15, 2019.

(52) U.S. Cl.
CPC ........ *A61B 5/14546* (2013.01); *A61B 5/6835* (2013.01); *A61B 2562/16* (2013.01); *A61B 2562/247* (2013.01)

(56) References Cited

U.S. PATENT DOCUMENTS

| | | | |
|---|---|---|---|
| 6,055,447 | A | 4/2000 | Weil et al. |
| 6,068,743 | A | 5/2000 | Fleckenstein |
| 7,811,433 | B2 | 10/2010 | Manoukian et al. |
| 8,062,221 | B2 | 11/2011 | Debreczeny et al. |
| 8,996,090 | B2 | 3/2015 | Anderson et al. |
| 11,013,434 | B2 * | 5/2021 | Pierskalla ............ A61B 5/6847 |
| 2002/0087057 | A1 | 7/2002 | Lovejoy et al. |
| 2002/0168296 | A1 | 11/2002 | Gambert |
| 2004/0003714 | A1 | 1/2004 | Bikson et al. |
| 2004/0006263 | A1 * | 1/2004 | Anderson ............ A61B 5/412 600/364 |
| 2005/0203362 | A1 | 9/2005 | Castillo et al. |
| 2006/0096871 | A1 | 5/2006 | Manoukian et al. |
| 2007/0142717 | A1 | 6/2007 | Lowery et al. |
| 2008/0011615 | A1 | 1/2008 | Omtveit |
| 2008/0039703 | A1 * | 2/2008 | Omtveit .................. A61B 5/01 600/353 |
| 2008/0319278 | A1 | 12/2008 | Omtveit et al. |
| 2010/0044226 | A1 | 2/2010 | Tonnessen et al. |
| 2012/0271131 | A1 | 10/2012 | Kling et al. |
| 2013/0274575 | A1 | 10/2013 | Winger et al. |
| 2016/0220833 | A1 | 8/2016 | Tan et al. |

OTHER PUBLICATIONS

Zhao et al., Non-invasive Detection of Oral Mucosal Carbon Dioxide Partial Pressure, Medical Gases Engineering, vol. 2, No. 2, Jun. 30, 2017 (abstract).
International Search Report and Written Opinion issued Aug. 25, 2021 in Application No. PCT/US2021/027261 (12 pages).
PCT International Search Report and Written Opinion mailed Jul. 29, 2020, for application No. PCT/US2020/033779, 15 pages.

* cited by examiner

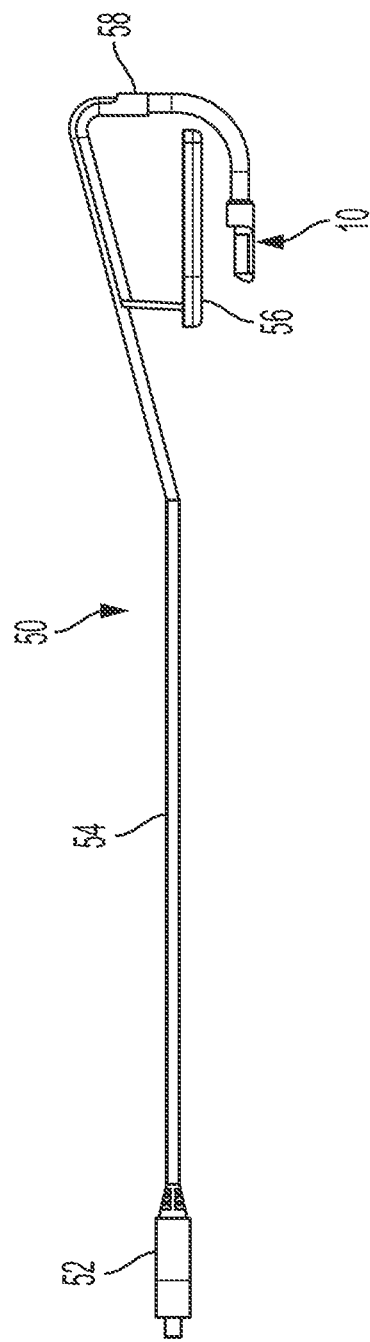
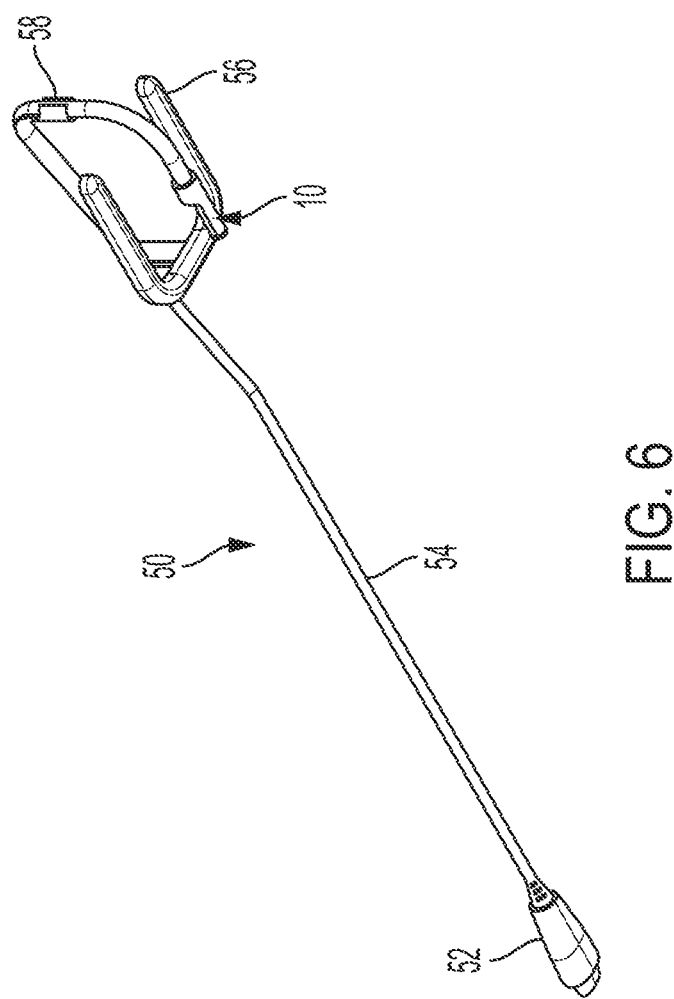
FIG. 5
FIG. 6

TISSUE PERFUSION SENSOR AND PLACEMENT DEVICE

CROSS REFERENCE TO RELATED APPLICATION(S)

This application claims benefit to U.S. application Ser. No. 16/879,199 filed May 20, 2020, now allowed, and U.S. Provisional Application No. 62/915,164, filed on Oct. 15, 2019. The entirety of the foregoing are incorporated herein by reference.

TECHNICAL FIELD

The disclosure relates to the field of sensors for measuring the partial pressure of carbon dioxide ($pCO_2$) in tissue. More particularly, the disclosure relates to sensors for measuring the partial pressure of carbon dioxide in mucosal tissue.

BACKGROUND

Very low blood flow, known as hypoperfusion can be caused by low blood volume, inadequate pumping action of the heart, or excessive widening (dilation) of blood vessels.

The body responds to such stress by reducing blood flow to less critical organs, such as the gastrointestinal tract, to spare blood for other, more critical organs. Thus, when there is a reduced flow of blood from the heart, the body directs a higher portion of blood to critical organs, such as the brain, which will not survive long without a continuous supply of blood, while restricting the flow of blood to less critical organs, whose survival is not as threatened by a temporary large reduction in blood flow.

For example, blood flow to the splanchnic vasculature, which supplies the stomach and intestines, and blood flow to the esophagus and oral/nasal cavity, is drastically reduced when there is reduced blood flow from the heart. For this reason, decreased blood flow to the splanchnic blood vessels is an indication of hypoperfusion in a patient. When hypoperfusion compromises intestinal mucosa, ischemia and gastric hypercapnia follow. These two clinical states can spur the release of bacteria and inflammatory substances into the splanchnic circulation, leading to sepsis and multiple organ dysfunction syndrome.

Carbon dioxide production, which is associated with metabolism, continues in tissues even during conditions of low blood flow. The concentration of carbon dioxide builds-up in tissues experiencing low blood flow because carbon dioxide is not rapidly carried away. This carbon dioxide build-up is exhibited by an increase in $pCO_2$ in organs. Therefore, hypoperfusion is commonly assessed by measuring $pCO_2$ at these sites.

Increases in $pCO_2$ may be measured throughout the body. Particularly, studies have shown that oral mucosal $pCO_2$ correlates well with gastric $pCO_2$ and thus oral mucosal constitutes an ideal site to measure $pCO_2$, especially if the sensing probe is isolated from ambient air and can be seated in a patient's mouth with minimal discomfort. Numerous studies have documented that both sublingual and buccal mucosal $pCO_2$ levels track circulatory stress in a quantitative fashion.

Measurements of $pCO_2$ have traditionally been taken with sensors having silicone membranes. Silicone membranes are useful because the large free volume in the polymer chain allows for rapid gas transport. Disadvantageously, however, silicone membranes also allow carboxylic acids, such as acetic acid, and other compounds found in saliva to pass through as well, which can interfere with $pCO_2$ measurements. For example, when acetic acid crosses the membrane into the sensor fluid, the pH is lowered and the conductivity of the fluid increases. Both alterations may falsely indicate an increase in carbon dioxide.

In addition, measurement of partial pressure of gases in tissue requires a sensor/tissue interface that is isolated from surrounding ambient air without application of excessive pressure. This has been attempted several ways, all which have limitations. First, measurement on the external epidermis has used adhesive patches and gels to isolate and capture the gas environment. This method is not practical for use on oral mucosal tissue which is inherently moist.

Secondly, handheld devices have been employed sublingually, with the tongue helping to seal off ambient exposure. This method is prone to errors because of the user dependent nature as well as not being practical for extended application. Furthermore, a method has been proposed by Anderson (U.S. Pat. No. 8,996,090) wherein the device is constructed with a material that deforms in response to pressure. The Anderson method is dependent not only on the material selection, but also the design of the applicator. Achieving the correct amount of flexibility so as not to create excessive pressure but still have enough pressure to keep the sensor in contact is problematic over the range of buccal tissue thickness found in adult patients. Normal buccal tissue thicknesses can range from about 7 mm to 20 mm. Maintaining contact without disturbing microcapillary blood flow requires pressure of no more than 25 mm Hg. Pressure in excess of 25 mm Hg can cause occlusion of blood flow that can cause errors in the measurement and damage to tissue.

Therefore, what is needed is a new design that allows for the rapid transmission of carbon dioxide while preventing the transmission of low molecular weight acids found in the saliva. What is also needed is a tissue placement device that is designed to hold and position the sensor against tissue, such as mucosal tissue.

BRIEF SUMMARY

The foregoing problems are addressed by the carbon dioxide sensor and tissue placement device in accordance with the disclosure.

In one or more scenarios, a sensor system for measuring partial carbon dioxide in a tissue is disclosed. In one aspect, the sensor system may include a sensor including a generally C-shaped in cross-section sensor cover, the sensor cover defining an opening on an underside thereof; a membrane body housed within the opening, the membrane body comprising an amorphous fluoroplastic, the membrane body including a first end and a second end and defining a chamber therewithin; a sensor body for coupling the membrane body to the sensor cover; two or more electrodes positioned within the membrane body; and a substantially electrolyte-free liquid contained within the membrane body chamber and surrounding the two or more electrodes. Optionally, the sensor may be responsive to an alternating electrical potential to measure the impedance of the substantially electrolyte-free liquid. In various embodiments, the lip of the generally C-shaped in cross-section sensor cover may be configured to shield the membrane body from end-tidal carbon dioxide.

In some implementations, the sensor system may also include a sensor placement device configured to position the membrane body against buccal tissue of a subject such that at least 40 to 50% of the membrane body contacts the buccal tissue. Optionally, the sensor placement device may include a sensor arm configured to couple with the sensor at a first end that is disposed on a first plane, a second arm including a deflecting surface that is on a second plane. The first plane is offset from the first plane by at least 5 mm. The sensor placement device may also include a beam for coupling a second end of the sensor arm to the second arm. The offset between the first plane and the second plane may be configured to receive the buccal tissue of the subject to position the membrane body against the buccal tissue. In certain embodiments, the membrane body may be either cylindrical or spherical. Alternatively and/or additionally, the deflecting surface may include a U-shaped portion formed by two arms that are equidistant to the sensor coupled to the first end of the sensor arm. In such embodiments, the sensor placement device may place the sensor against the buccal tissue without air gaps and without applying pressure in excess of 25 mm Hg by folding the buccal tissue over the membrane body via the two arms of the U-shaped portion. Optionally, the beam of the sensor placement device may include a ratcheting element configured to change the offset between the second plane and the first plane.

In some other scenarios, a sensor placement device for placing a sensor for measuring partial pressure of carbon dioxide ($pCO_2$) against buccal tissue of a subject is disclosed. The sensor placement device may include a sensor arm configured to couple with the sensor at a first end that is on a first plane and a second arm on a second plane that includes a U-shaped deflecting surface, and a beam for coupling a second end of the first sensor arm to the second arm. The first plane may be offset from the second plane that is offset that is configured to receive the buccal tissue of the subject to position a membrane body of the sensor against the buccal tissue by folding the buccal tissue over the membrane body via the U-shaped deflecting surface. Optionally, the offset may be at least about 5 mm. Additionally and/or alternatively, the beam may include a ratcheting element configured to change the offset between the second plane and the first plane.

In various embodiments, the sensor placement device may be configured to place the sensor against the buccal tissue without air gaps and without applying pressure in excess of 25 mm Hg. Optionally, the U-shaped deflecting surface may include two arms that are equidistantly placed from the sensor when coupled to the first end of the sensor arm.

In certain other scenarios, a method for determining partial pressure of carbon dioxide ($pCO_2$) in tissue is disclosed. The method may include providing a sensor that may include a membrane body housed within an opening formed by a C-shaped sensor cover, placing the sensor proximate to a buccal tissue of a subject without air gaps and without applying pressure in excess of 25 mm Hg using a sensor placement device, and measuring $pCO_2$ in the buccal tissue. The membrane body may include a first amorphous fluoroplastic and may form an enclosed chamber including a first end and a second closed end.

In certain embodiments, the method may also include coupling the sensor to a first end of a sensor arm of the sensor placement device. The first end may be on a first plane that is offset from a second plane that includes a second arm of the sensor placement device that includes a U-shaped deflecting portion. Optionally, the method may include controlling the offset between the first plane and a second plane to be about 5 mm. Additionally and/or alternatively, the method may include controlling the offset between the first plane and a second plane to be such that two arms of the U-shaped deflecting portion fold the buccal tissue over the membrane without applying pressure in excess of 25 mm Hg. Controlling the offset may include moving the second arm relative to the first end using a ratcheting element included in the sensor placement device.

The method may, optionally, include shielding the membrane body from end-tidal carbon dioxide by providing a lip in the generally C-shaped in cross-section sensor cover and positioning the second closed end adjacent the lip.

These and other aspects of the disclosure will be disclosed in the Detailed Description and appended claims.

BRIEF DESCRIPTION OF THE DRAWINGS

For a better understanding of the disclosure, and to show how the same may be carried into effect, reference will now be made, by way of example, to the accompanying drawings, in which:

FIG. 5 is a side view of a sensor placement device for positioning the carbon dioxide sensor against a buccal surface.

FIG. 6 is a perspective view of the sensor placement device for positioning the carbon dioxide sensor against a buccal surface.

DETAILED DESCRIPTION

Figure 1:
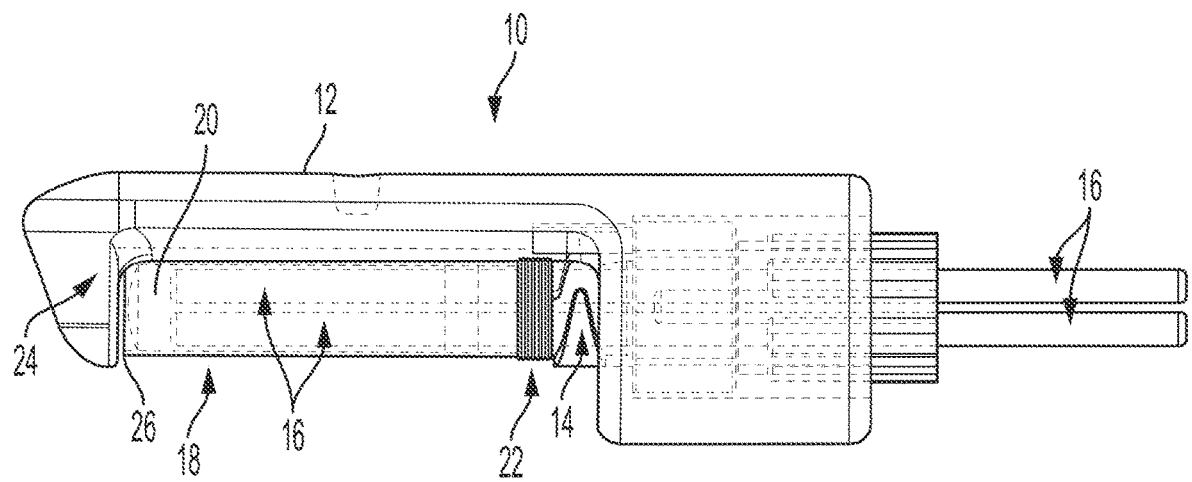
FIG. 1 is a side view of the carbon dioxide sensor in accordance with the disclosure.
Figure 2:
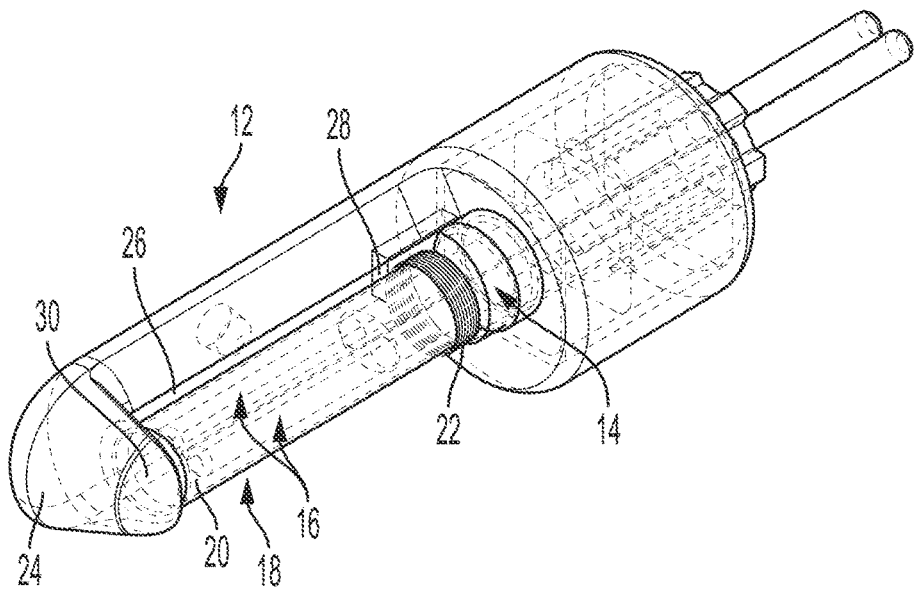
FIG. 2 is a perspective view of the carbon dioxide sensor in accordance with the disclosure.
Figure 3:
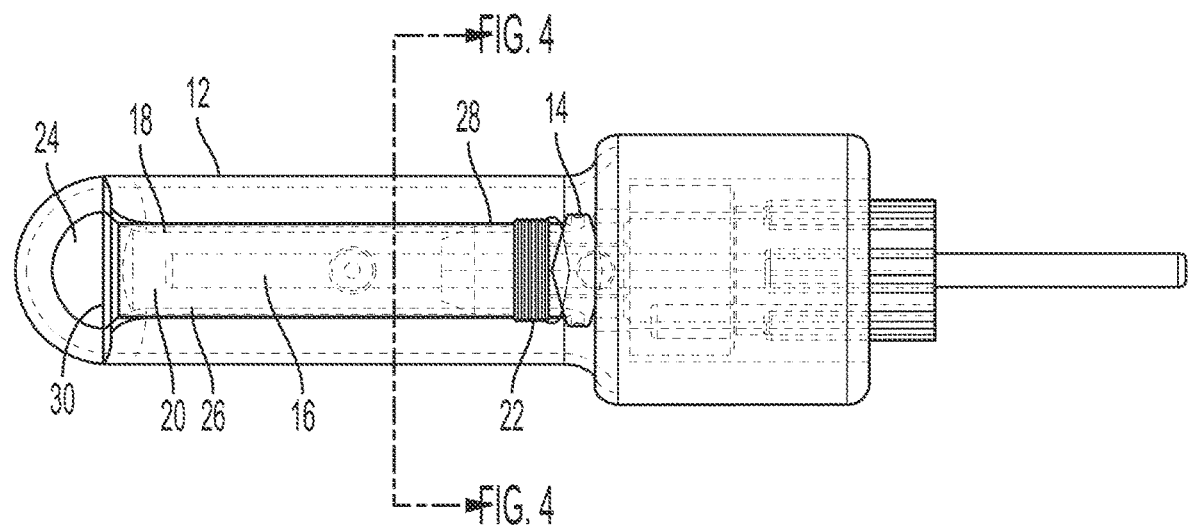
FIG. 3 is a bottom view of the carbon dioxide sensor in accordance with the disclosure.
Figure 4:
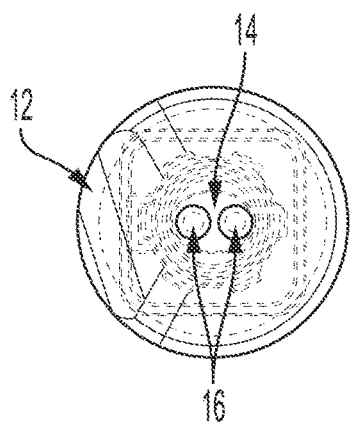
FIG. 4 is a cross-sectional view of the carbon dioxide sensor in accordance with the disclosure taken along line A-A of FIG. 3.

In the drawings, like reference numerals designate identical or corresponding parts throughout the several views.

As used herein, the words "a," "an" and the like generally carry a meaning of "one or more," unless stated otherwise. The term "plurality", as used herein, is defined as two or more than two. The term "another", as used herein, is defined as at least a second or more. The terms "including" and/or "having", as used herein, are defined as comprising (i.e., open language).

Reference throughout this document to "one embodiment", "certain embodiments", "an embodiment", "an implementation", "an example" or similar terms means that a particular feature, structure, or characteristic described in connection with the example is included in at least one example of the present disclosure. Thus, the appearances of such phrases or in various places throughout this specification are not necessarily all referring to the same example. Furthermore, the particular features, structures, or characteristics may be combined in any suitable manner in one or more examples without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Further, in individual figures, some components/features shown are drawn to scale to exemplify a particular implementation while other components and features are not drawn to scale.

Referring now to FIG. 1 a side view of the carbon dioxide sensor in accordance with the disclosure is shown. The sensor 10 broadly includes sensor cover 12, sensor body 14, pair of electrodes 16, membrane body 18, sensor fluid 20 and winding filament 22.

The sensor cover may be constructed of a thermoplastic such as polyethylene, polypropylene, polystyrene and polycarbonate. The sensor cover 12 generally covers and houses the sensor body 14 and membrane body 18. Sensor cover 12 is shaped such that it forms an opening 26 on an underside thereof for housing the sensor body 14 and membrane body 18. One such shape is a generally C-shaped in cross section. Sensor cover 12 includes a downwardly projecting lip 24 that shields the membrane body 18 from end tidal carbon dioxide when in use. Advantageously, the sensor cover 12 permits tissue contact for greater than 40% to 50% of membrane body 18. The sensor cover 12 is designed to cover the portion of the membrane body 18 that is not in contact with tissue. Because the sensor placement device 58 is designed to fold the tissue around one side of the sensor, a cylindrical shape membrane body 18 is used. To cover the portion of the membrane body 18 that is not in contact with tissue, the inside surface of the sensor cover 12 may have a C-shaped cross section in order to minimize any gaps (dead-space that acts as a sink that can slow down the response of the sensor). In addition, the sides of the sensor cover 12 may be tapered to allow for better tissue contact.

Sensor body 14 may also be constructed of a thermoplastic such as polyethylene, polypropylene, polystyrene and polycarbonate. Sensor body 14 may be constructed of the same thermoplastic as sensor cover 12 or may comprise a different thermoplastic. Preferably, for manufacturing cost efficiencies sensor body 14 is constructed of the same thermoplastic as sensor cover 12. Sensor body 14 is configured to hold and align electrodes 16 securely in place within membrane body 18. Sensor body 14 provides an attachment point for membrane body 18 and for securing the winding filament 22 to provide a secure attachment between the sensor body and the membrane body 18. Those of skill in the art will appreciate that other attachments may be used such as snap-on, adhesives, bonding and crimping.

Pair of electrodes 16 are constructed of stainless steel and are configured to receive an alternating electrical potential from a supply source. Those of skill in the art will appreciate that metals other than stainless steel may also be used. Electrodes 16 are positioned securely in place by sensor body 14. Electrodes 16 are housed within membrane body 18 and positioned in sensor fluid 20. Those of skill in the art will appreciate that two or more electrodes may be used and still fall within the scope of the disclosure. For example, conductance can be measured with two, three, or four electrodes.

Membrane body 18 is positioned in opening 26 of sensor cover 12. Membrane body 18 comprises a hollow tube defining a chamber therewithin. The membrane body 18 is substantially impermeable to low molecular weight carboxylic acids, including acetic acid, which is found in salvia and can compromise precise readings of carbon dioxide levels in oral mucosa. Membrane body 18 may be constructed of fluoropolymer resins such as an amorphous fluoroplastic. Suitable amorphous fluoroplastics include Teflon AF 2400 (available from The Chemours Company). Teflon AF 2400 is known to have exceptional permeability for carbon dioxide. However, heretofore, it has been undiscovered that amorphous fluoroplastics, such as Teflon AF 2400, have a structure with a large free volume in the polymer chain that allows for rapid carbon dioxide transport but also does not permit carboxylic acids, such as acetic acid, to transport across it. Teflon AF 2400 has a carbon dioxide permeability of 2800 Barrer units as compared to polytetrafluoroethylene which has a carbon dioxide permeability of 120 Barrer units. Alternatively, polymethylpentenes (available from Mitsui Chemicals America) may be used in place of an amorphous fluoroplastic. Membrane body 18 is open at a first end 28 to allow for filling with sensor fluid 20 prior to attachment to the sensor body 14, which then seals it. A second end 30 is sealed with Teflon AF 1600, which has a much lower carbon dioxide transmission rate than AF 2400. Teflon AF 1600 easily fuses to membrane body 18 and provides a leak free environment. The second end of the tube is situated against lip 24 so it does not contact tissue and does not need to be permeable to carbon dioxide. Sensor fluid 20 may be a substantially electrolyte-free liquid such as pharmaceutical-grade purified water (USP grade water). In some aspects of the disclosure distilled water may also be used.

Winding filament 22 is used to secure the membrane body 18 to sensor body 12. Adhesive may be used to bond and reinforce the winding filament 22.

Figure 7:
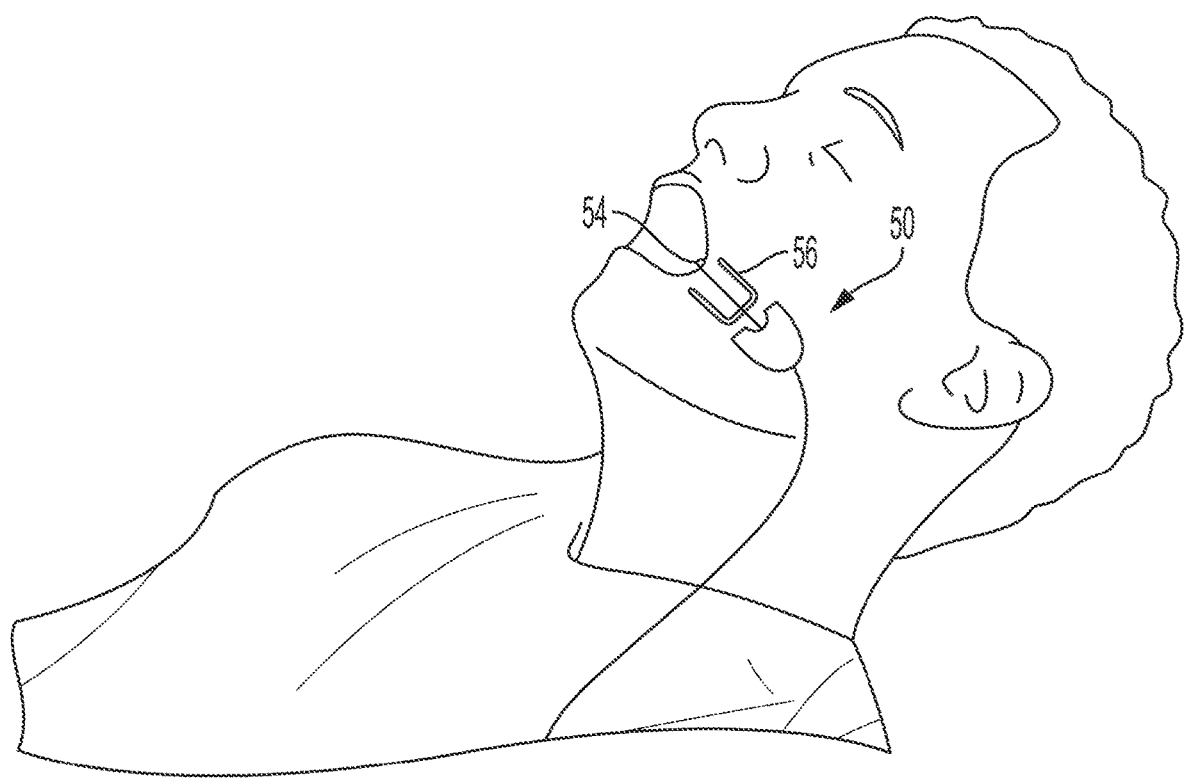
FIG. 7 is a perspective view of the sensor placement device being used on a patient.

Referring now to FIGS. 5-7 a sensor placement device 50 for secure placement of the sensor 10 against a buccal surface is illustrated. The sensor placement device broadly includes proximal end 52, elongate middle portion 54 and distal end 56. Proximal end 52 is adapted to operably couple to electronics for reading and displaying the $pCO_2$ measurements. Distal end 56 includes U-shaped ridge 56 for positioning the device 50 against the outside surface of the cheek and the sensor on the inside of the cheek. Sensor 10 is attached to the positioning device 50 by arm 58.

In operation to be used to measure tissue $pCO_2$ in the oral cavity, the sensor 10 is deployed in a sensor placement device 50 configured to fit the human cheek. As shown, sensor placement device 50 with sensor 10 is a disposable device. Using the elongate middle portion, a user may insert the sensor 10 into the mouth of a subject and position a U-shaped ridge at the distal end 56 to the outside surface of the cheek such that the cheek of the subject is positioned between the arm 58 that includes the sensor 10 and the U-shaped ridge of the distal end 56. This, in turn, holds the sensor 10 against the buccal surface of the cheek and between the two arms of the U-shaped ridge such that the two arms of the U-shaped ridge fold the buccal tissue (i.e., the inside of the cheek) against the membrane (e.g., cylindrical, dome-shaped, etc.) of the sensor 10 for providing optimal contact without excessive pressure application. The device 50 is designed (i.e., the spacing between the sensor plane and the U-shaped ridge is configured) so the sensor 10 is held in direct contact with the buccal tissue without air gaps and without applying pressure in excess of 25 mm Hg and preferably less than 20 mm Hg, less than 15 mm Hg, or the like. Excess pressure can disturb blood flow and alter the level of $pCO_2$. A person of skill in the art will understand that the U-shaped ridge may be any suitable shape such as a, a V-shape, a c-shape, a square loop-shape, a triangular loop shape, an oval loop shape, or the like.

The response time of the sensor 10 for measuring the $pCO_2$ may be influenced by the ratio of surface area (that allows analyte to pass through) to the volume of the sensor. If the sensor is positioned next to the mucosal surface (no pressure applied), a cylindrical shaped membrane of sensor will have only a small percentage of the membrane directly in contact with the tissue (tangential) leading to an increase in response time. If suitable pressure is applied to push the cylindrical surface into the tissue, about 40 to 50% of the membrane surface may contact the tissue as the surface is deflected away from the pressure. However, the applied pressure must be carefully modulated so as not to disturb microcapillary blood flow and introduce an error in the measurements. The sensor placement device 50 of the current disclosure is configured such that it folds the buccal tissue about the cylindrical membrane surface of the sensor 10 to achieve this greater tissue contact without applying excessive pressure. Optionally, the sensor cover may also be tapered away from the membrane surface to allow for the higher percentage of tissue contact.

Sensor cabling (not shown) attaches the sensor placement device with sensor to electronic equipment (not shown) that provides an alternating electrical potential to the sensor 10 and measures the impedance of the sensor fluid 20 contained within membrane body 18. The equipment is calibrated to the sensor response curve and an algorithm calculates the $pCO_2$ value from the temperature-adjusted conductance signal. The sensor response curve is determined by measuring the sensor signal in two reference solutions of known $pCO_2$ levels; a low $pCO_2$ reference and a "normal" $pCO_2$ reference. The "normal" solution approximates the $pCO_2$ of healthy, well perfused tissue. From this data, the slope of the response curve is determined. Values of $pCO_2$ are then calculated from the signal difference from the "normal" reference solution. The calculated $pCO_2$ values are then displayed graphically and numerically on an integrated display. The electronic device is configured as a standalone patient monitoring device, but those of skill in the art will appreciate that it can be integrated into a multi-modal patient monitoring system.

Figure 8:
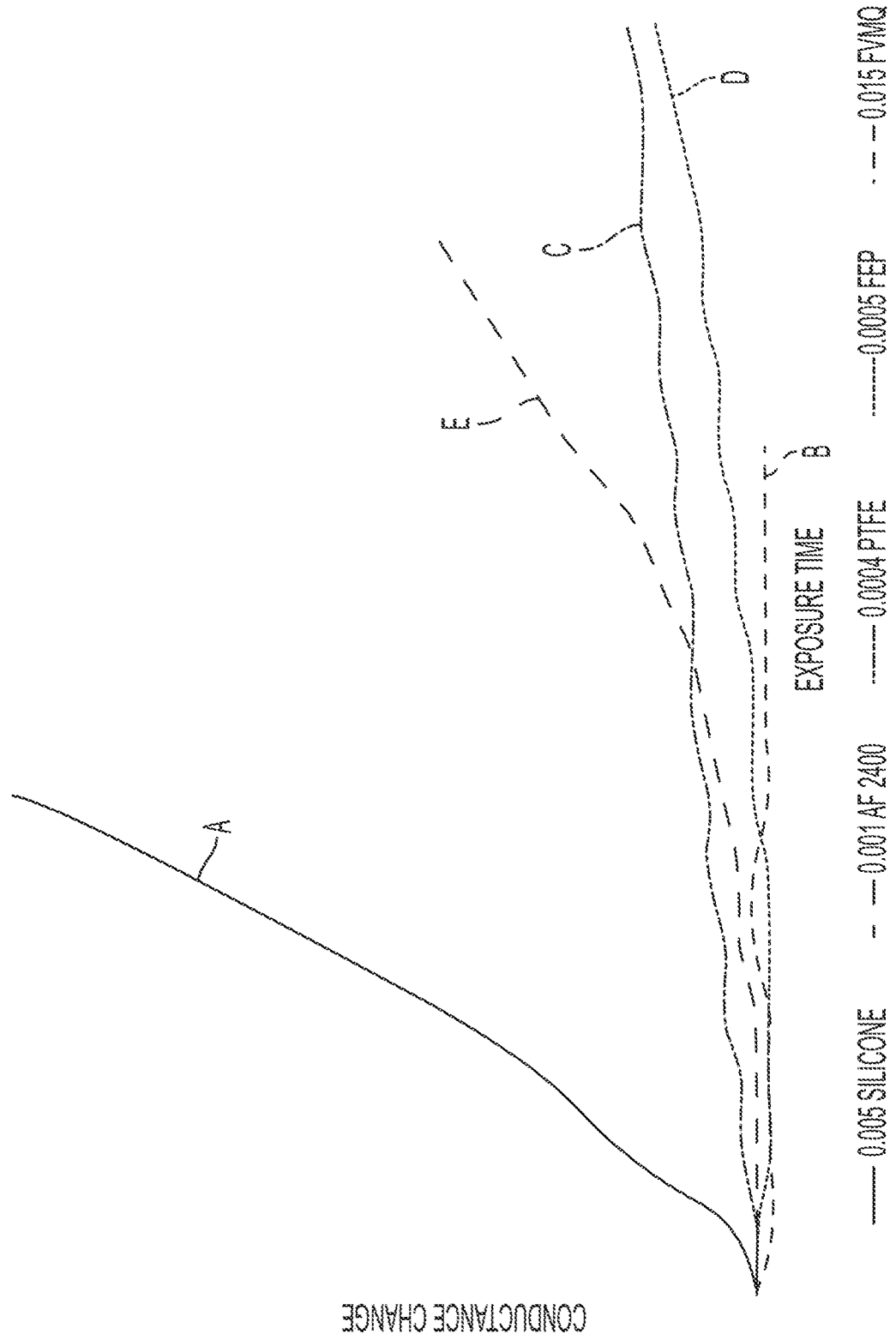
FIG. 8 is a graph illustrating a comparison of various membrane materials exposure to acetic acid.
Figure 9:
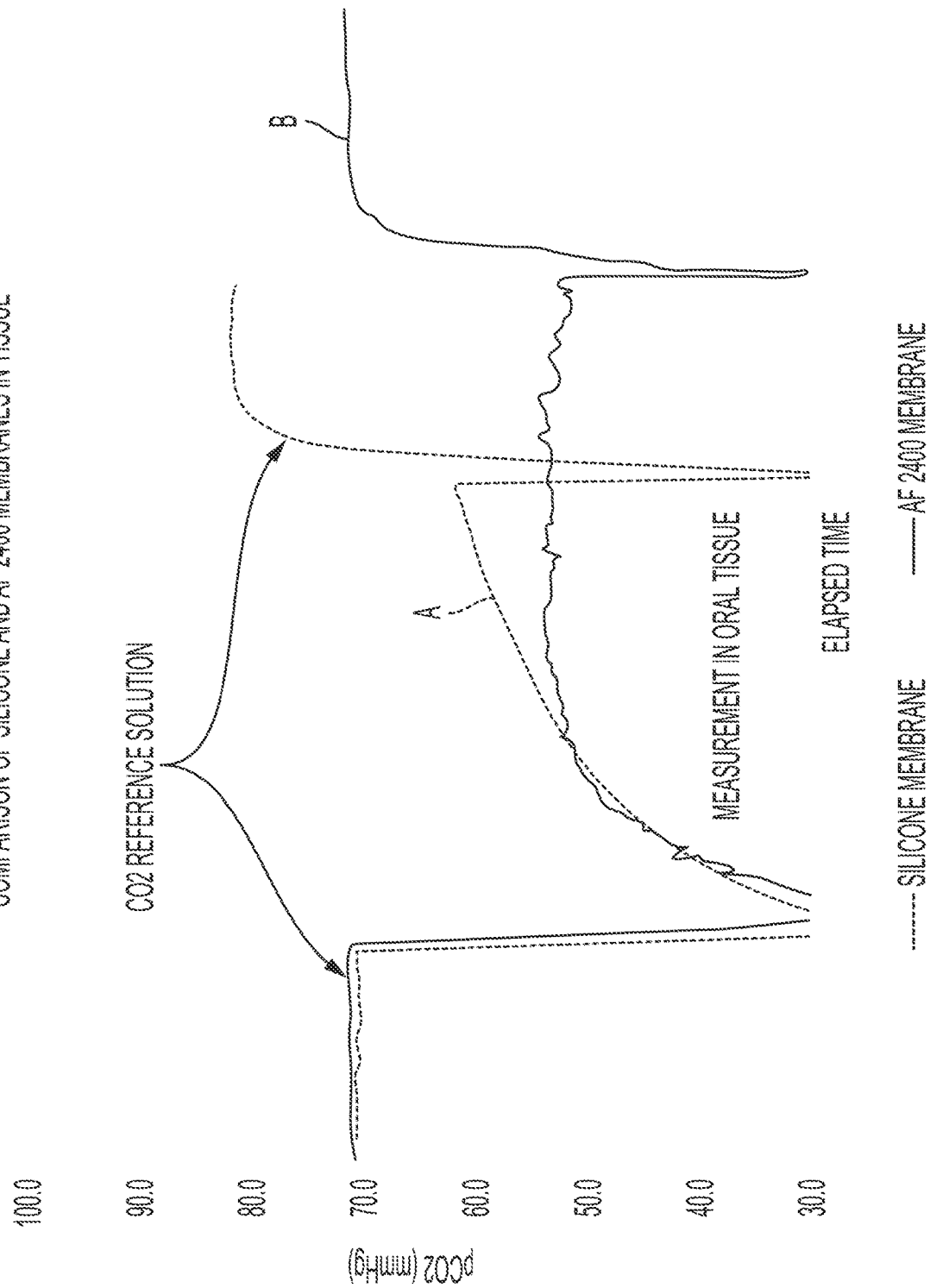
FIG. 9 is a graph illustrating a comparison of silicone and amorphous fluoroplastic membranes in tissue.

Referring now to FIGS. 8 and 9 comparison data will now be discussed. FIG. 8 graphically illustrate the results of an in vitro study of several membrane materials. These membranes were exposed to 8 mM acetic acid solution and the conductance change was monitored in an effort to determine suitability for application in the oral cavity. Membrane thicknesses were chosen based on the ability to achieve a reasonable carbon dioxide permeation rates. The results demonstrate the superiority of the Teflon AF 2400. FIG. 8 shows a comparison of potential membrane materials evaluated at thicknesses necessary to provide comparable response times wherein A—0.005" PDMS Silicone; B—0.001" Teflon AF2400; C—0.0004" PTFE; D—0.0005" FEP; and E—0.015" FVMQ Silicone.

A conductance probe was cover with the material being tested and then exposed to 8 mM Acetic acid (in the physiological range for saliva). Of the materials tested, the typical membrane material (A—PDMS Silicone) is the most permeable to acetic acid. In 60 minutes, the conductance has increased by 1 uS/cm due to acetic acid crossing PDMS silicone membrane. Membrane E (0.015" FVMQ Silicone) allowed an increase of 0.12 uS/cm during that time while Membrane C (0.0004" PTFE) and membrane D (0.0005" FEP) showed better resistance to acetic acid penetration, ~0.05 uS/cm over 60 minutes. However, membrane B (0.001" Teflon AF2400) allowed no detectable increase in conductance over that same time period.

FIG. 9 graphically illustrates an overlay of in vivo studies of a sensor constructed with a silicone membrane compared to a sensor constructed with a Teflon AF 2400 membrane. A reference solution was measured pre- and post-exposure to oral mucosal tissue. The results demonstrate the contamination that can occur with the use of a silicone membrane, as well as demonstrating the suitability of Teflon AF 2400. FIG. 9 depicts a comparison of tissue data collected with a PDMS silicone membrane (A) and a Teflon AF2400 membrane (B). Reference values were measured in a water tonometered with 10% CO2 (pCO2=~70 mmHg). Sensors were then positioned into a subjects buccal tissue and data was collected for about 60 minutes. The graph indicates that the Teflon AF2400 membrane sensor stabilized at ~53 mmHg pCO2, while the PDMS silicone membrane sensor continued to rise past 60 mmHg $pCO_2$ and never stabilized. Sensors were placed back into the tonometers. The Teflon AF2400 membrane sensor returned to the pre-tissue exposure value while the Silicone membrane sensor indicates an error of ~10 mmHg pCO2 correlating to increased signal caused by the acetic acid contamination.

Figure 10:
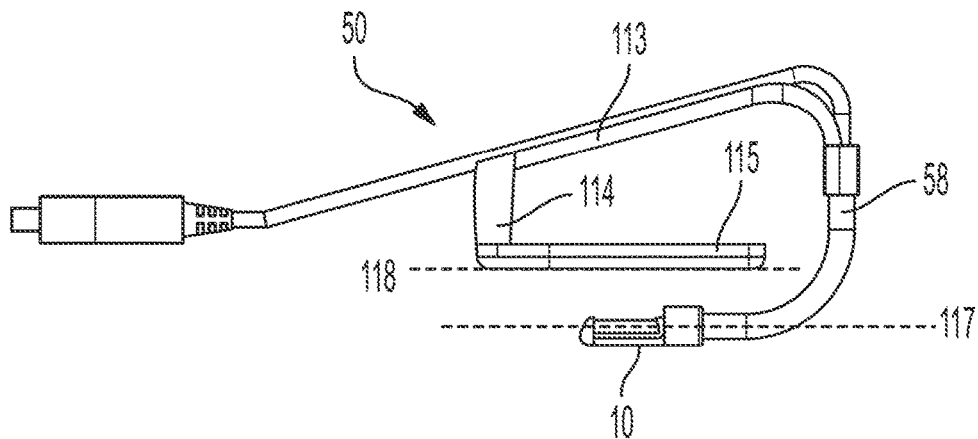
FIG. 10 is a side view of the sensor placement device in accordance with the disclosure.
Figure 11:
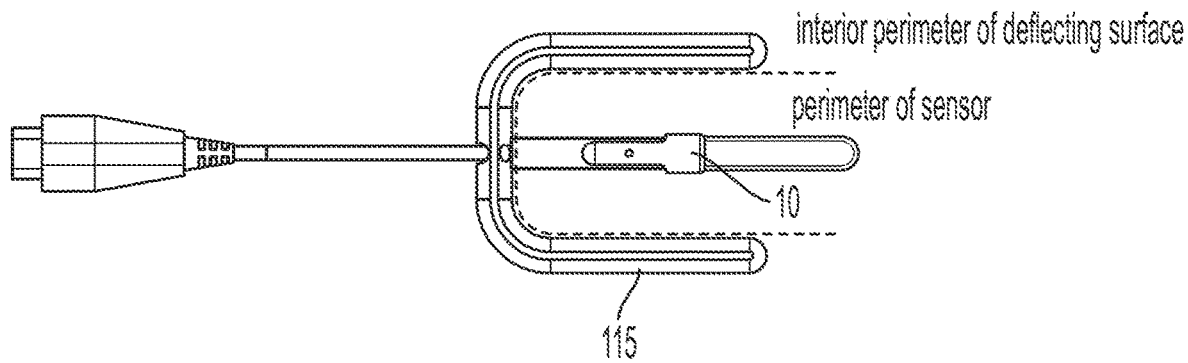
FIG. 11 is a bottom view of the sensor placement device in accordance with the disclosure.
Figure 12:
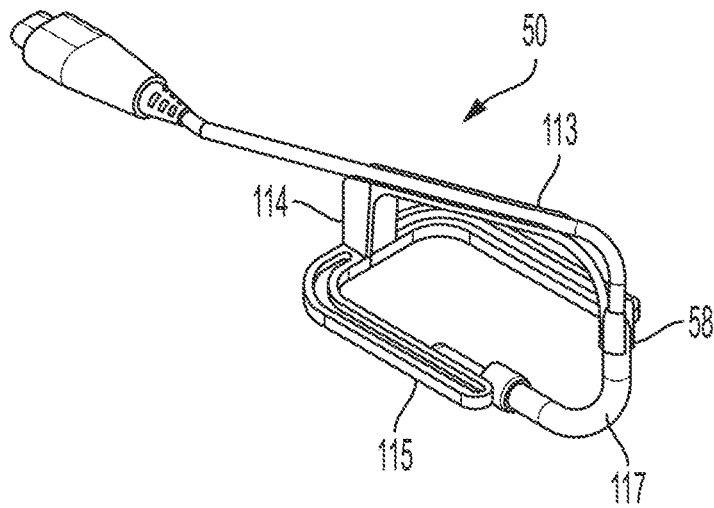
FIG. 12 is a perspective view of the sensor placement device in accordance with the disclosure.

Referring now to FIG. 10 a side view of the sensor placement device 50 in accordance with the disclosure is shown. The device 50 positions sensor 10 against tissue. The sensor placement device 50 broadly includes curved sensor arm 58, angled beam 113, connecting post 114, and deflecting surface 115. The sensor placement device 50 provides ample space so as not to squeeze the tissue against which it is positioning the sensor 10. Rather, the sensor placement device 50 (e.g., the two arms of the U-shaped portion) utilizes the flexibility of the buccal tissue to fold the tissue around the cylindrical membrane of the sensor 10 to achieve 40-50% or greater contact with the tissue, as hereinafter disclosed. The device 50 includes a sensor arm 58 on one plane and two arms equidistant distant from the sensor arm 58 that together form the U-shaped deflecting surface 115 on a separate plane such that the sensor 10 is positioned between the two arms of the U-shaped deflecting surface 115, as best seen in FIG. 11. This way the deformability of the device 50 material is not required.

Sensor 10 measures an analyte or characteristic indicative of microcirculatory blood flow. The membrane of the sensor 10 is preferably cylindrical or domed or has a suitable shape characteristic that adapts to having tissue folded over it. If the sensor 10 measures a gas, the sensor 10 requires a sensor cover 12 to protect the sensor from exposure to ambient and end-tidal gases. Sensor arm 58 may be constructed of a thermoplastic such as engineered thermoplastic polyurethane, polyethylene, polypropylene, polystyrene and polycarbonate. Sensor arm 58 attaches to beam 113 that in turn attaches to the top of post 114. In this manner, sensor arm 58 is configured to hold sensor 10 on the sensor plane 117. Beam 113 and post 114 may also be constructed of a thermoplastic such as engineered thermoplastic polyurethane, polyethylene, polypropylene, polystyrene and polycarbonate.

Deflecting surface 115, similarly constructed of a thermoplastic such as engineered thermoplastic polyurethane, polyethylene, polypropylene, polystyrene and polycarbonate, is attached to the bottom of post 114. In this manner the bottom of deflecting surface 115 defines deflecting surface plane 118. To ensure contact on the low end of normal buccal tissue thickness (approximately 7 mm), sensor arm plane 117 and deflecting surface plane 118 may be less than about 5 mm apart, about 4-6 mm apart, about 5 mm apart, about 3-5 mm apart, or the like such that the pressure exerted does not exceed about 25 mm Hg that can cause occlusion of blood flow and errors in the measured $pCO_2$. The line of sight above sensor 10 is ideally free of obstructions for at least 20 mm, at least about 10 mm, at least about 15 mm, about 15-25 mm, or the like to prevent pinching of tissue between surfaces of the device 50. Optionally, to adapt to thicker buccal tissue, the interior perimeter of deflecting surface 115 may be offset from the perimeter of sensor 10 (as shown in FIG. 11) by about 15 mm to about 20 mm, about 16 mm to about 19 mm, about 17 mm to about 18 mm, about 15 mm to about 20 mm, or the like.

Figure 13:
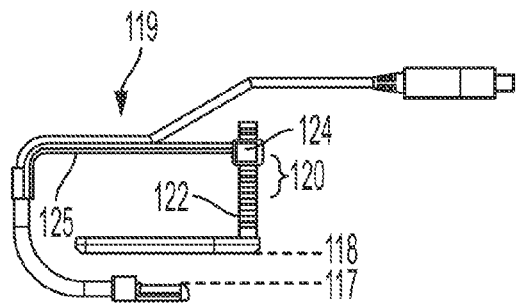
FIG. 13 is a side view of an alternative ratcheting version of the sensor placement device in accordance with the disclosure set to a 5 mm separation.
Figure 14:
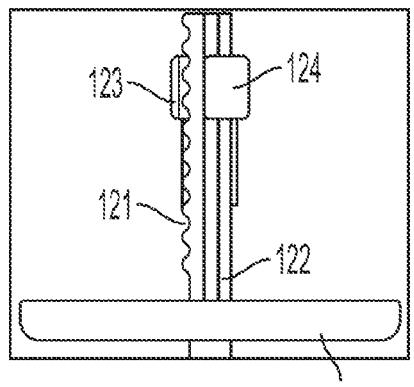
FIG. 14 is a partial view of an alternative ratcheting version of the sensor placement device in accordance with the disclosure set to a 5 mm separation.
Figure 15:
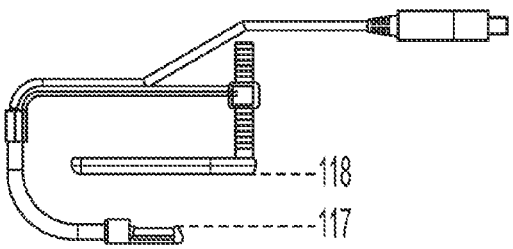
FIG. 15 is a side view of an alternative ratcheting version of the sensor placement device in accordance with the disclosure set to a 10 mm separation.
Figure 16:
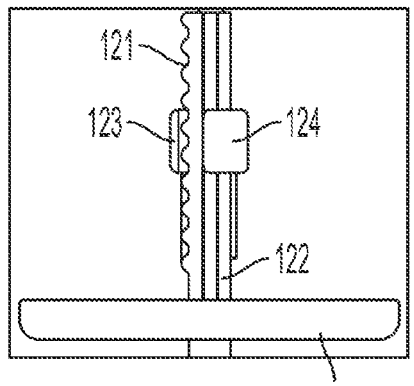
FIG. 16 is a partial view of an alternative ratcheting version of the sensor placement device in accordance with the disclosure set to a 10 mm separation.

FIG. 13 illustrates a sensor placement device 119 that is similar to that disclosed in FIG. 10; however includes a ratcheting element 120 configured for modifying and controlling the separation between the sensor plane 117 and deflecting surface plane 118. Ratcheting element 120 is shown in partial view FIG. 14 corresponding to a separation of about 5 mm between sensor plane 117 and deflecting surface plane 118. Ratcheting element 120 may include serrations 121 found on post 122 and complementary ratchet tooth 123 on beam head 124. Beam head 124 is further attached to beam 125 and has alignment features that mate with post 122. The beam head may move up and down the post 122 via engagement of the serrations 121 with the complementary ratchet tooth 123. FIG. 15 and FIG. 16 illustrate an increase in the separation between sensor plane 117 and deflecting surface plane 118 via ratcheting feature 120. In this manner, device 119 may be adaptable to a wide range of buccal tissue thickness. Other mechanisms for adjusting the spacing between the sensor plane 117 and the deflecting surface plane 118 are within the scope of this disclosure.

Although the invention has been described with reference to certain aspects and embodiments, those of skill in the art will appreciate that changes may be made in form and detail without departing from the spirit and scope of the invention.

We claim:

1. A sensor system for measuring partial pressure of carbon dioxide ($pCO_2$) in tissue, the sensor system comprising:
    a sensor comprising:
        a generally C-shaped in cross-section sensor cover defining an opening bounded on a top by an underside of the sensor cover and bounded on a distal end by a lip;
        a membrane body housed within the opening, the membrane body comprising a first amorphous fluoroplastic, the membrane body forming an enclosed chamber including:
            a first end, and
            a second closed end situated against the lip;
        a sensor body disposed at the first end for coupling the first end to the sensor cover;
        two or more electrodes extending from the first end and positioned within the enclosed chamber; and
        a substantially electrolyte-free liquid contained within the enclosed chamber and in contact with the two or more electrodes; and
    a sensor placement device configured to facilitate placement of the sensor in a subject, the sensor placement device comprising a U-shaped portion configured to fold tissue over the membrane body of the sensor, wherein the U-shaped portion resides in a plane that is offset from another plane in which the sensor resides when the sensor is coupled to the sensor placement device.

2. The sensor system of claim 1, wherein the sensor placement device is configured to position the membrane body against buccal tissue of the subject such that at least 40 to 50% of the membrane body contacts the buccal tissue.

3. The sensor system of claim 1, wherein the sensor is responsive to an alternating electrical potential to measure the impedance of the substantially electrolyte-free liquid.

4. The sensor system of claim 1, wherein the lip of the generally C-shaped in cross-section sensor cover is configured to shield the membrane body from end-tidal carbon dioxide.

5. A sensor system for measuring partial pressure of carbon dioxide ($pCO_2$) in tissue, the sensor system comprising:
    a sensor comprising:
        a generally C-shaped in cross-section sensor cover defining an opening bounded on a top by an underside of the sensor cover and bounded on a distal end by a lip;
        a membrane body housed within the opening, the membrane body comprising a first amorphous fluoroplastic, the membrane body forming an enclosed chamber including:
            a first end, and
            a second closed end situated against the lip;
        a sensor body disposed at the first end for coupling the first end to the sensor cover;
        two or more electrodes extending from the first end and positioned within the enclosed chamber;
    a substantially electrolyte-free liquid contained within the enclosed chamber and in contact with the two or more electrodes; and
    a sensor placement device configured to position the membrane body against buccal tissue of a subject such that at least 40 to 50% of the membrane body contacts the buccal tissue;
    wherein the sensor placement device comprises:
        a sensor arm configured to couple with the sensor at a first end, the first end being on a first plane;
        a second arm comprising a surface configured to fold the buccal tissue over the membrane body, the second arm being on a second plane that is offset from the first plane by at least 5 mm; and
        a beam for coupling a second end of the sensor arm to the second arm, wherein the offset between the first plane and the second plane is configured to receive the buccal tissue of the subject to position the membrane body against the buccal tissue.

6. The sensor system of claim 5, wherein the membrane body is cylindrical or spherical.

7. The sensor system of claim 5, wherein the surface comprises a U-shaped portion formed by two arms that are equidistant to the sensor coupled to the first end of the sensor arm.

8. A sensor system of claim 7, wherein the sensor placement device is configured to place the sensor against the buccal tissue without air gaps and without applying pressure in excess of 25 mm Hg by folding the buccal tissue over the membrane body via the two arms of the U-shaped portion.

9. The sensor system of claim 5, wherein the beam comprises a ratcheting element configured to change the offset between the second plane and the first plane.

10. A sensor placement device for placing a sensor for measuring partial pressure of carbon dioxide ($pCO_2$) against buccal tissue of a subject, the sensor placement device comprising:
   a sensor arm configured to couple with the sensor at a first end, the first end being on a first plane;
   a second arm comprising a U-shaped surface, the second arm being on a second plane that is offset from the first plane; and
   a beam for coupling a second end of the first sensor arm to the second arm, wherein the offset between the first plane and the second plane is configured to receive the buccal tissue of the subject to position a membrane body of the sensor against the buccal tissue by folding the buccal tissue over the membrane body via the U-shaped surface.

11. The sensor placement device of claim 10, wherein the offset is at least about 5 mm.

12. The sensor placement device of claim 10, wherein the beam comprises a ratcheting element configured to change the offset between the second plane and the first plane.

13. A sensor placement device of claim 10, wherein the sensor placement device is configured to place the sensor against the buccal tissue without air gaps and without applying pressure in excess of 25 mm Hg.

14. The sensor placement device of claim 10, wherein the U-shaped surface comprises two arms that are equidistantly placed from the sensor when coupled to the first end of the sensor arm and that form a U-shape.

15. A method for determining partial pressure of carbon dioxide ($pCO_2$) in tissue, the method comprising:
   providing a sensor comprising a membrane body housed within an opening formed by a C-shaped sensor cover, the membrane body comprising a first amorphous fluoroplastic, the membrane body forming an enclosed chamber including:
      a first end, and
      a second closed end;
   placing, using a sensor placement device, the sensor proximate to a buccal tissue of a subject without air gaps and without applying pressure in excess of 25 mm Hg;
   using a U-shaped portion of the sensor placement device to fold the buccal tissue over the membrane body of the sensor, wherein the U-shaped portion resides in a plane that is offset from another plane in which the sensor resides; and
   measuring, using the sensor, the $pCO_2$ in the buccal tissue.

16. The method of claim 15, further comprising shielding the membrane body from end-tidal carbon dioxide by providing a lip in the generally C-shaped in cross-section sensor cover and positioning the second closed end adjacent the lip.

17. A method for determining partial pressure of carbon dioxide ($pCO_2$) in tissue, the method comprising:
   providing a sensor comprising a membrane body housed within an opening formed by a C-shaped sensor cover, the membrane body comprising a first amorphous fluoroplastic, the membrane body forming an enclosed chamber including a first end and a second closed end;
   coupling the sensor to a first end of a sensor arm of the sensor placement device, the first end being on a first plane that is offset from a second plane that includes a second arm of the sensor placement device, wherein the second arm includes a U-shaped portion configured to fold the buccal tissue over the membrane body;
   placing, using a sensor placement device, the sensor proximate to a buccal tissue of a subject without air gaps and without applying pressure in excess of 25 mm Hg; and
   measuring, using the sensor, the $pCO_2$ in the buccal tissue.

18. The method of claim 17, further comprising controlling the offset between the first plane and a second plane to be about 5 mm.

19. The method of claim 17, further comprising controlling the offset between the first plane and a second plane to be such that two arms of the U-shaped deflecting portion fold the buccal tissue over the membrane without applying pressure in excess of 25 mm Hg.

20. The method of claim 19, wherein controlling the offset comprises moving the second arm relative to the first end using a ratcheting element included in the sensor placement device.

* * * * *